United States Patent
Glasford et al.

(10) Patent No.: US 9,504,625 B2
(45) Date of Patent: Nov. 29, 2016

(54) VIBROACOUSTIC WATER SYSTEM

(75) Inventors: Barry D. Glasford, Cedarburg, WI (US); Mary J. Reid, Sheboygan, WI (US); David Ison, Elliotsburg, PA (US)

(73) Assignee: KOHLER CO., Kohler, WI (US)

( * ) Notice: Subject to any disclaimer, the term of this patent is extended or adjusted under 35 U.S.C. 154(b) by 465 days.

(21) Appl. No.: 12/408,777

(22) Filed: Mar. 23, 2009

(65) Prior Publication Data

US 2009/0241254 A1    Oct. 1, 2009

Related U.S. Application Data

(60) Provisional application No. 61/041,157, filed on Mar. 31, 2008.

(51) Int. Cl.
*A61H 33/00* (2006.01)
*A61H 23/02* (2006.01)
*A61N 5/06* (2006.01)

(52) U.S. Cl.
CPC ...... *A61H 23/0218* (2013.01); *A61H 23/0236* (2013.01); *A61H 33/005* (2013.01); *A61H 33/0087* (2013.01); *A61H 2033/0083* (2013.01); *A61H 2201/10* (2013.01); *A61H 2201/5048* (2013.01); *A61N 2005/0663* (2013.01)

(58) Field of Classification Search
CPC ............. A61H 33/087; A61H 33/60; A61H 33/0091; A61H 2033/0079; A61H 23/0236; A61H 23/0245; A61H 23/0218; H04R 1/028; A47K 3/10; A47K 3/001

USPC ...... 601/1, 2, 46, 47, 55, 76, 154, 157, 159, 601/160, 48–49, 155, 158, 166, 167; 4/541.1; 607/85

See application file for complete search history.

(56) References Cited

U.S. PATENT DOCUMENTS

| | | | |
|---|---|---|---|
| 3,585,991 A | 6/1971 | Balamuth | |
| 4,354,064 A * | 10/1982 | Scott | 381/326 |
| 4,507,816 A | 4/1985 | Smith, Jr. | |
| 4,575,882 A | 3/1986 | Diamond | |
| 4,884,574 A | 12/1989 | Hardie et al. | |
| 4,942,868 A | 7/1990 | Vago | |
| 5,101,810 A | 4/1992 | Skille et al. | |
| 5,178,134 A | 1/1993 | Vago | |
| 5,339,804 A | 8/1994 | Kemp | |

(Continued)

FOREIGN PATENT DOCUMENTS

| | | |
|---|---|---|
| DE | 7728423 U | 12/1977 |
| DE | 8105025 | 9/1981 |

(Continued)

OTHER PUBLICATIONS

Clark Synthesis, Tactile Sound 101, http://www.clarksynthesis.com, May 16, 2005 (Printed Feb. 20, 2009).

(Continued)

*Primary Examiner* — Kari Petrik
(74) *Attorney, Agent, or Firm* — Foley & Lardner LLP

(57) ABSTRACT

A vibroacoustic system has a shell for containing water to which transducers are mounted. Multi-channel input signals cause the transducers to drive the shell to effect distinct, but coordinated tactile and aural stimuli providing a unique combined vibratory and auditory water experience for the user.

20 Claims, 14 Drawing Sheets

(56) References Cited

U.S. PATENT DOCUMENTS

| | | | |
|---|---|---|---|
| 5,645,578 | A | 7/1997 | Daffer et al. |
| 5,702,353 | A * | 12/1997 | Guzzini et al. .................. 601/2 |
| 5,741,317 | A * | 4/1998 | Ostrow .............. A61H 23/0245 607/81 |
| 5,898,957 | A | 5/1999 | Hansen et al. |
| 6,001,073 | A | 12/1999 | Schmidt et al. |
| 6,251,088 | B1 | 6/2001 | Kaufman et al. |
| 6,523,191 | B2 | 2/2003 | Lahay et al. |
| 6,544,165 | B1 | 4/2003 | McNew |
| 6,868,563 | B1 | 3/2005 | Hutchings et al. |
| 2002/0025050 | A1 | 2/2002 | Macey |
| 2002/0148038 | A1 | 10/2002 | Gardenier et al. |
| 2003/0061653 | A1 | 4/2003 | Carlet |
| 2004/0016051 | A1 | 1/2004 | Gardenier et al. |
| 2004/0073996 | A1 | 4/2004 | Hill |
| 2005/0091739 | A1 | 5/2005 | Lerma |

FOREIGN PATENT DOCUMENTS

| | | |
|---|---|---|
| DE | 4022114 A1 | 1/1992 |
| DE | 4241312 A1 | 6/1994 |
| DE | 4312115 A1 | 10/1994 |
| DE | 4435879 A1 | 4/1996 |
| DE | 19545549 | 9/1996 |
| DE | 29508669 U1 | 1/1997 |
| DE | 19814499 A1 | 10/1999 |
| DE | 19843379 A1 | 3/2000 |
| DE | 19902875 C1 | 7/2000 |
| DE | 19903460 C2 | 8/2000 |
| DE | 10100457 C1 | 10/2002 |
| DE | 202004018797 U1 | 4/2005 |
| EP | 0335851 A2 | 10/1989 |
| EP | 0355299 B1 | 2/1990 |
| EP | 0595783 A2 | 5/1994 |
| EP | 0604742 A1 | 7/1994 |
| EP | 0645130 A2 | 3/1995 |
| EP | 0645131 B1 | 3/1995 |
| EP | 0651987 A2 | 5/1995 |
| EP | 0986985 B1 | 3/2000 |
| EP | 1093783 B1 | 4/2001 |
| EP | 1192969 B1 | 4/2002 |
| EP | 1298259 A2 | 4/2003 |
| JP | S55131743 | 9/1980 |
| JP | S57173060 | 10/1982 |
| JP | S57175360 | 10/1982 |
| JP | S58010050 | 1/1983 |
| JP | S58025130 | 2/1983 |
| JP | S58025131 | 2/1983 |
| JP | S58025132 | 2/1983 |
| JP | S58025133 | 2/1983 |
| JP | S58028636 | 2/1983 |
| JP | S58069562 | 4/1983 |
| JP | S59008329 | 1/1984 |
| JP | 5912902 | 4/1984 |
| JP | H02098776 | 8/1990 |
| JP | 03 015423 A | 1/1991 |
| JP | 04241600 | 8/1992 |
| JP | H04108533 | 9/1992 |
| JP | 07000469 | 1/1995 |
| JP | 733769 | 8/1995 |
| JP | 08229091 | 9/1996 |
| JP | 2000254190 | 9/2000 |
| JP | 2003106651 | 4/2003 |
| JP | 2003180784 | 7/2003 |
| JP | 2004105569 | 4/2004 |
| JP | 2004344284 | 12/2004 |
| WO | 98/27923 | 7/1998 |
| WO | WO 9827923 A1 * | 7/1998 ......... A61H 23/0236 |
| WO | 99/25256 | 5/1999 |
| WO | 99/52582 | 10/1999 |
| WO | 02/058618 A1 | 8/2002 |
| WO | 02/064075 A2 | 8/2002 |
| WO | 02/096152 A1 | 11/2002 |
| WO | 03/039365 A2 | 5/2003 |

OTHER PUBLICATIONS

Deuel, Stephen, "Olav Skille's Vibroacoustic Therapy Frequency CDs," http://www.vibroacoustic.org/FrequencyInfor/Olav.htm, May 16, 2005.

Lightning Sound Relayer Company, "Examples of frequency ranges in music when evaluating sound theories concerning speaker crossovers," http://www.lightningsound.net/examples.html, May 16, 2005 (Feb. 6, 2005 version from www.web.archive.org, printed Feb. 23, 2009).

Skille, Olav, "Vibroacoustic Manual (English version 1990)," http://members.tripod.com/~quadrillo/VAT/e_manual-2.html, May 16, 2005 (Printed Feb. 23, 2009).

Hydrotherapy Tubs (pp. 70-71), www.spa-central.com.

Hot Spring Portable Spas, Sensational Sound, http://www.hotspring.com/Spa Showroom Hot Tub/spa audio stereo music.html, Mar. 25, 2008.

Deuel, Stephen, Vibroacoustic.org, Vibroacoustic Tactile Sound Massage Table—VAT Equipment.

Watkins Manufacturing Corporation, Hot Spring Portable Spas, SpAudio: The World's Greatest Underwater Symphony.

Olav Skille, Trilax Center, New Software for VAT on CD, Jul. 7, 2004.

Brewer, Chris, Life Sounds, Vibroacoustic Research Reports and Summaries.

Wigram, Anthony Lewis, "The Effects of Vibroacoustic Therapy on Clinical and Non-Clinical Populations, Thesis Submitted for the Degree of Doctor of Philosophy, St. Georges Hospital Medical School, London University," http://members.tripod.com/~quadrillo/VAT/tonyphd.com, May 16, 2005 (Printed Feb. 23, 2009).

Deuel, Stephen, "Olav Skille's Vibroacoustic Therapy Frequency CDs," http://www.vibroacoustic.org/FrequencyInfor/Olay.htm, Mar. 25, 2008.

Olav Skille, Olav Skille's New Hompage entrance, http://members.tripod.com/quadrillo/, Feb. 23, 2009.

PCT International Search Report and Written Opinion, Jul. 1, 2009, PCT/US2009/001933.

Third Office Action for Chinese Application No. 200980120060.4 with English translation, mail date Aug. 13, 2013.

Third Office Action for Mexican Application No. MX/a/2010/010705.

Third Office Action for Mexican Application No. MX/a/2010/010716.

Final Office Action in U.S. Appl. No. 12/407,410 dated Jul. 8, 2013.

* cited by examiner

VIBROACOUSTIC WATER SYSTEM

CROSS-REFERENCE TO RELATED APPLICATION

This application claims priority based on U.S. provisional application 61/041,157 filed Mar. 31, 2008.

STATEMENT OF FEDERALLY SPONSORED RESEARCH OR DEVELOPMENT

Not applicable.

BACKGROUND OF THE INVENTION

The present invention relates to vibroacoustics. More particularly, it relates to a vibroacoustic water or bathing system that produces distinct, controlled auditory and vibratory experiences.

The use of a bath tub shell (e.g., a bathtub) as an acoustic speaker to reproduce music is generally known. U.S. Pat. No. 6,523,191 discloses an acoustically active hot tub that has a plurality of transducers affixed to blocks embedded in the shell of the hot tub. The audio transducers transform electrical signals from a music source into vibrations that are transmitted to the shell of the hot tub, causing the shell to vibrate. The hot tub shell vibrates within a range of frequencies suitable for transmitting audible frequencies generally associated with music. Thus, users can listen to music while aerated water is circulating within the hot tub by pumps and jets.

However, the techniques discussed above do not use the hot tub shell to create two discrete effects. The transducers merely produce an audible sound for users of the hot tub. Furthermore, the jets used in the hot tub of U.S. Pat. No. 6,523,191 detract from, if not completely eliminate, any incidental vibrations that might be felt by the bathers as a result of the transducers reproducing the music.

German patent DE19902875 presents another example of a tub used as an acoustic speaker. The focus of this reference is to improve the efficient transmission of the mechanical oscillations of a transducer to the shell of a tub, improving the ability of the shell to act as an acoustic speaker. However, as with U.S. Pat. No. 6,523,191, German patent DE19902875 simply uses the shell as a pseudo speaker, without consideration of input signals or the effect of the output signals beyond the reproduction of audible sounds.

The use of a single transducer mounted adjacent a tub to vibrate the water, and thus the bather, is also generally known. U.S. Pat. No. 3,585,991 discloses a transducer mounted in an energy coupling relationship with one wall of a tub. The transducer coupled to the wall produces a series of energy waves through the water via the single wall of the tub, whereas a separate speaker not coupled to the tub shell (e.g., headphones or an ambient sound system) is included to produce music.

Thus, U.S. Pat. No. 3,585,991 does not use the tub as an acoustic speaker, but only uses a single wall for vibratory purposes and has a separate speaker to produce audible music. In addition, the disclosure instructs to create a visible movement of the water with a whirlpool type unit, which would clearly detract from the impact of the energy waves traveling through the water.

European patent application publication EP0651987 also incorporates transducers mounted through openings in a tub wall to allow ultrasonic waves to transmit directly into the tub. Thus, the tub is not used as a speaker, but merely as an isolated mount for the transducers having a gasket between the tub and the transducer. Furthermore, the tub incorporates a hydro-massage (e.g., water jets) in addition to the transducers, again detracting from the ultrasonic waves.

A divide has been established in the related art between using a bathing enclosure to produce either vibrations or audio because of the challenges inherent in creating controlled vibratory and auditory experiences. Thus, it was unexpected that the challenges would be overcome to create a vibroacoustic plumbing fixture having a shell driven by two distinct signals capable of creating an auditory experience and a vibratory experience having differing wave characteristics.

SUMMARY OF THE INVENTION

In one aspect the invention provides a vibroacoustic water system. The system includes a shell for containing water and two sets of transducers mounted in energy transmitting relation to the shell. One set of transducers uses an audile input signal having an audile wave characteristic to drive the shell and effect an aural stimulus. The other set of transducers drives the shell to effect a tactile stimulus in the water different from the aural stimulus using a multi-channel vibratile input signal having a vibratile wave characteristic different from the audile wave characteristic.

In another aspect one, and preferably both, sets of transducers are arranged to allow for panning or other spatially control or variation of the aural and tactile stimuli with respect to the shell. For example, the tactile stimulus can pan in a biorhythmic pattern. The tactile stimuli can be directed to one or more sides, quadrants or other portions of the shell so as to provide location specific treatment. The same is true for the aural stimulus. The panning or spatial variation of the aural and tactile stimuli can occur in a perceptibly random manner or can be coordinated with each other so that by working in concert the aural and tactile stimuli can provide a desired combined vibratory and auditory experience that, for example, tends to sooth or invigorate the user.

With a sufficient quantity of the transducers and by suitably controlling the amplitude and/or frequency for each of the audile and vibratile signals, the associated transducers can create a spatial "center", or the perception thereof, for each of the aural and tactile stimuli.

The spatial control and resolution of the aural and tactile stimuli can be affected by the number of distinct input signal channels as well as the positional placement and quantity of transducers. For example, four transducers receiving separate input signals and spaced apart on intersecting perpendicular axes can allow for varying of the spatial center of the sound or vibration generally within the two dimensions of the plane defined by the axes. Increasing the number of transducers and input signals increases the resolution of the spatial control.

By using multiple sets of multiple transducers and input signals, such as separate vibratile and audile transducer sets, the spatial centers of the vibration and sound can be manipulated either independent of or in coordination with one another to provide a desired overall vibratory and auditory experience. For instance, the spatial centers of the aural and tactile stimuli can be controlled to reside either at a common area or at different areas. The spatial centers can overlap and provide a vibroacoustic experience at a location specific site, for example, at a particular body part of a bather, or the spatial centers can move in concert with one another, either in the same or similar paths or in any divergent linear or non-linear paths that provides the desired effect.

To further enhance the effect on the user without the sensation of following a set track, routine or program, the vibratory and auditory experience can be achieved through the use of audile and vibratile wave characteristics that are non-melodic, non-repetitive or both.

These and still other aspects and advantages of the present invention will be apparent from the detailed description and drawings. What follows are merely preferred example embodiments of the present invention. To assess the full scope of the invention the claims should be looked to.

DETAILED DESCRIPTION OF EXAMPLE EMBODIMENT(S)

Figure 1:
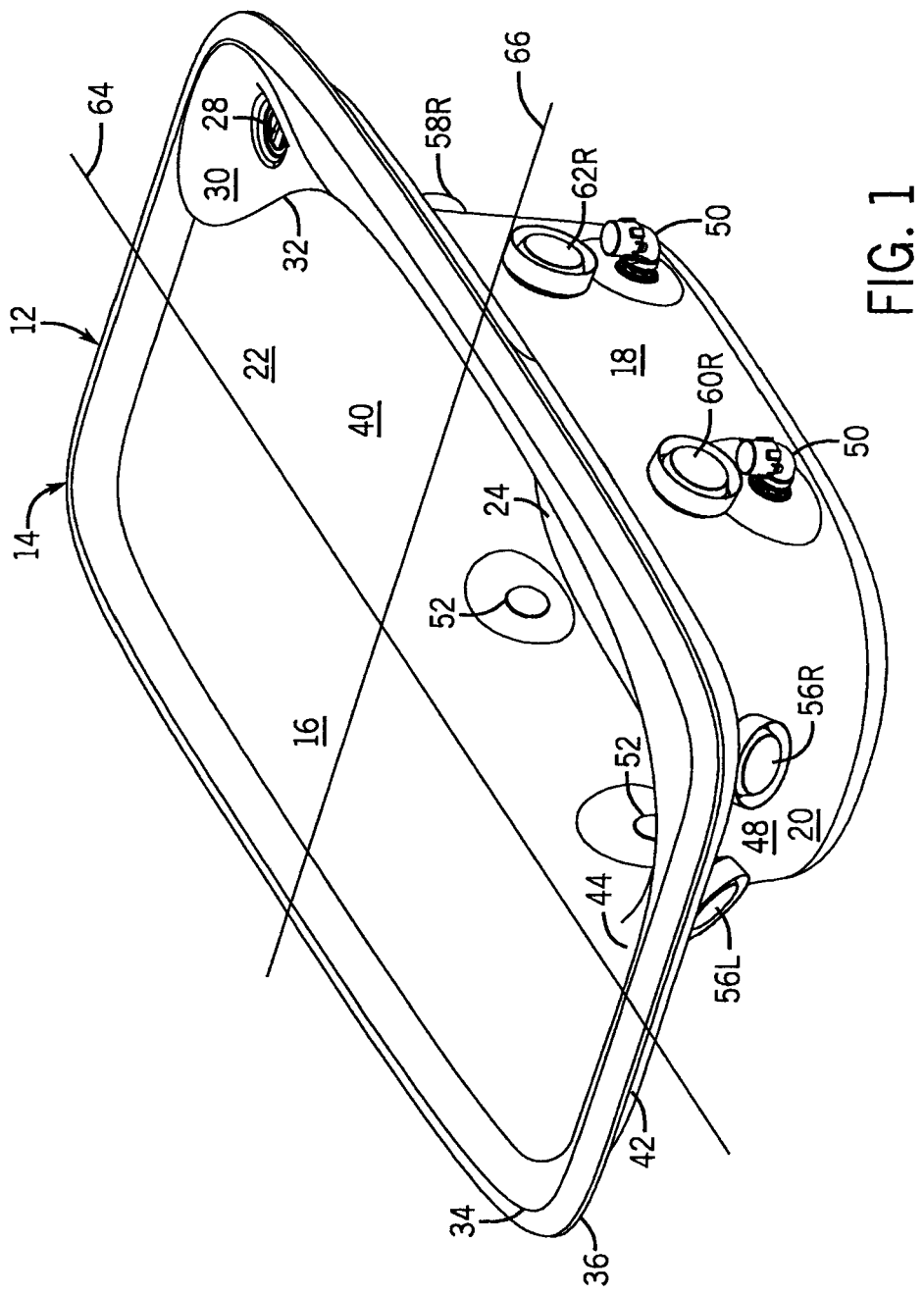
FIG. 1 is an isometric view showing a vibroacoustic water or bathing system in accordance with the present invention.

The present invention provides a vibroacoustic water or bathing system in the form of a plumbing fixture 12 (preferably a bathtub) capable of simultaneously producing and effecting to a bather 11 both controlled auditory and vibratory experiences.

The auditory experience primarily imparts to the bather 11 an aural stimulus that is produced by a shell 14 driven in response to an audile signal that incorporates wave characteristics under a traditional musical framework. The musical framework includes typical musical elements such as tones centered on a particular key and harmonies related to the key. The auditory experience preferably includes an audible melody of aural focus that is heard by the bather 11. The auditory experience is preferably propagated through a gaseous medium, such as air, to the bather 11 and essentially effects an aural stimulus.

The vibratory experience primarily imparts a generally tactile stimulus to the bather 11 that is also produced by a shell 14 driven in response to a vibratile signal that incorporates wave characteristics that are distinct from at least one of the wave characteristics of the audile signal. The tactile vibrations of the vibratory experience generally include non-melodic wave characteristics specifically created to achieve a controlled vibratory experience that is effected via a tactile stimulus. The wave characteristics of the vibratory experience preferably communicate a non-discernable, ancillary experience that do not establish a temporal framework, meaning that a typical adult bather can be subjected to the same vibratile signal on multiple occasions and not be able to readily consciously distinguish the beginning, middle, end, or other temporal relationships within a particular vibratory experience.

The vibratory experience is preferably propagated through a liquid medium, such as water, to the bather 11 and generally effects a tactile stimulus, such as a deep massaging experience. Furthermore, the vibratory experience preferably includes controlled application of vibrations produced by the shell 14 to manipulate the location and intensity of the vibratory experience.

The vibroacoustic plumbing fixture 12, more specifically the shell 14, has been "tuned" to customize the auditory and vibratory experiences produced by the shell 14 and propagated through the air and water to effect the respective aural and tactile stimuli. The shell 14 is preferably tuned to a desired key so as to respond favorably to the predominant frequencies of the particular key. A favorable shell 14 response generally means that the shell 14 exhibits minimal vibratory damping in the preferred range of frequencies at which the shell 14 is configured to operate to enhance the desired wave characteristics. The relationships between the shell 14 and desired auditory and vibratory experiences are established by relating the frequency response of the shell 14 (e.g., the natural frequency and harmonics of the shell 14) to the wave characteristics of the desired auditory and vibratory experiences.

An example vibroacoustic plumbing fixture 12 is shown in FIG. 1. The fixture or system 12 includes a shell 14, such as a bathtub, shower stall, sink, or other similar basin, that is preferably made of fiberglass reinforced plastic, but may be made of a variety of other materials and combinations of materials, such as acrylic, metal, porcelain, and the like. The frequency response of the shell 14 is partially dependent on the materials and geometry of the shell 14. For example, depending on the geometry, cast iron can be too dense and include too much mass to establish a preferred vibroacoustic plumbing fixture. However, with the appropriate geometry and structure, a cast iron shell may be used in accordance with the present invention. The geometry and materials of the shell 14 are preferably customized to respond favorably in the desired frequency range given the specifics of each application and the wave characteristics of the auditory and vibratory experiences.

The shell 14 generally includes a left side wall 16 offset from a right side wall 18, a head wall 20 offset from a foot wall 22, and a base 24 connecting the walls 16, 18, 20, 22. The shell 14 is typically partially filled with water via a spout controlled by a valve (not shown). A drain 26 is formed in the base 24 to allow the water to be emptied from the shell 14 when not in use. Additionally, an overflow drain 28 is seated in an overflow ledge 30 to ensure that water does not rise above the waterline 32 and breach a plane 34 defined by a rim 36 of the shell 14.

The foot end 38 of the shell 14 may include a foot rest portion 40 having a contoured surface configured to engage and support the feet of a user when in the shell 14. Additionally, the head end 42 may include a head pocket 44 formed above a backrest portion 48 of the head wall 20. The backrest portion 48 is sloped and contoured to provide the bather 11 with a reclined position once in the shell 14.

The head pocket 44 may take on a variety of configurations. However, each is dimensioned and sized such that when the head of a bather 11 rests in the head pocket 44, the ears of bather 11 are essentially below the plane 34, and preferably, above the waterline 32. Keeping the ears below the rim 36 of the shell 14 and above the waterline 32 alters the aural stimulus produced by the shell 14 that is propagated through the air (described in greater detail below). The head pocket 44 may alternatively be configured such that the ears are located below the waterline 32. Again, the aural stimulus effected by the auditory and vibratory experiences is altered.

The vibroacoustic plumbing fixture 12 may also include a series of chromotherapy devices 50 mounted to the shell 14 that are generally synchronized with the vibrations of the shell 14. The chromotherapy devices 50 may be comprised of multi-colored light emitting diodes, filament bulbs, fiber optic strands, and the like, and are housed behind translucent or transparent lenses 52. The chromotherapy devices 50 can be mounted by any technique known to those skilled in the art. Furthermore, the location and quantity of the chromotherapy devices 50 can be altered as desired.

The vibroacoustic bathing system 12 includes a plurality of transducers mounted in energy coupling relation to the shell 14. The transducers drive and vibrate the shell 14 thereby effecting the auditory and vibratory experiences. While the example embodiment will be described with reference to electromagnetic transducers, the transducers may be of any type capable of transforming an input signal into a corresponding mechanical vibration. In the example embodiment, the transducers are preferably electromagnetic Rolen-Star Audio Transducers.

Figure 2:
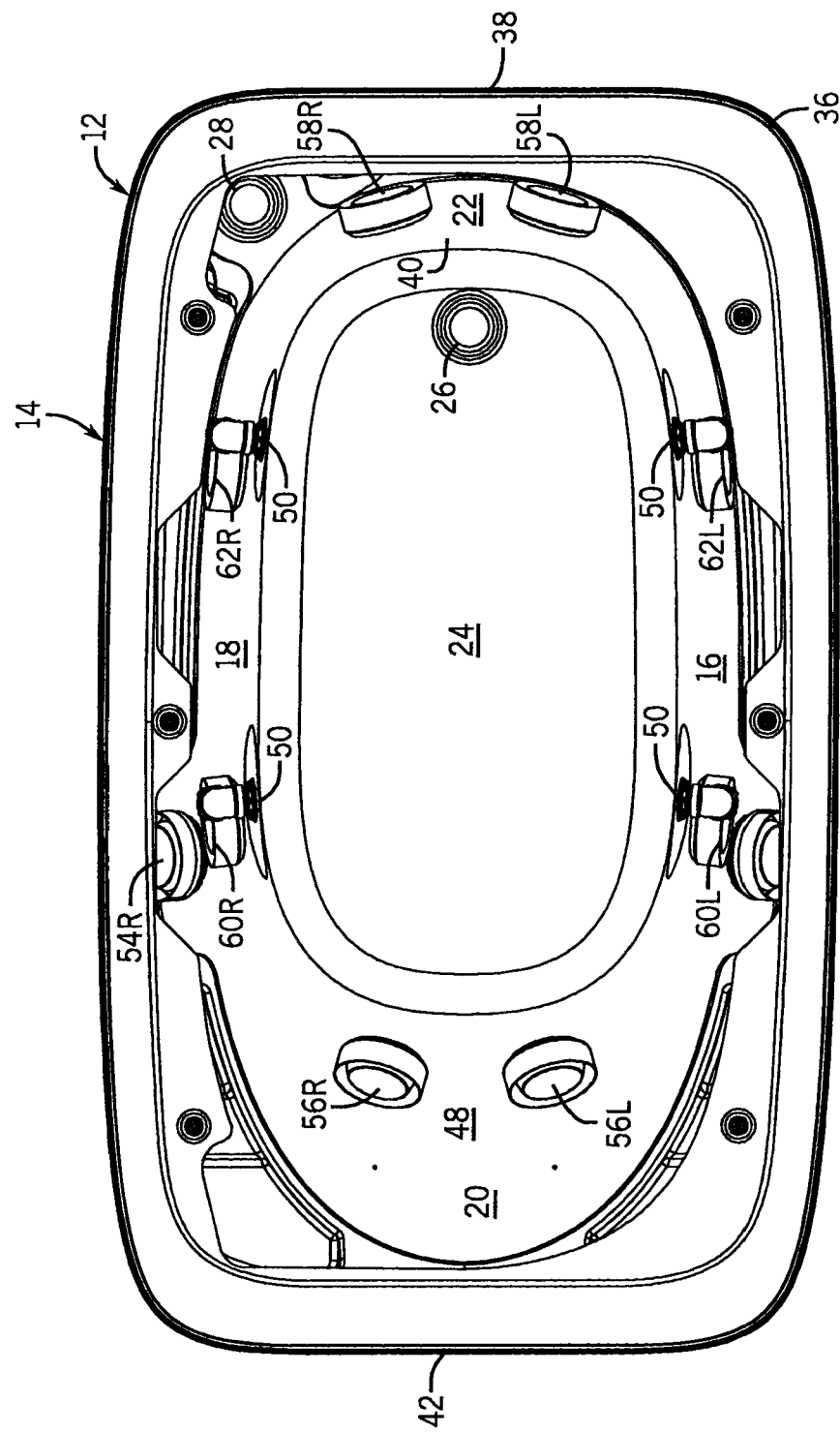
FIG. 2 is a bottom elevation view thereof.
Figure 3:
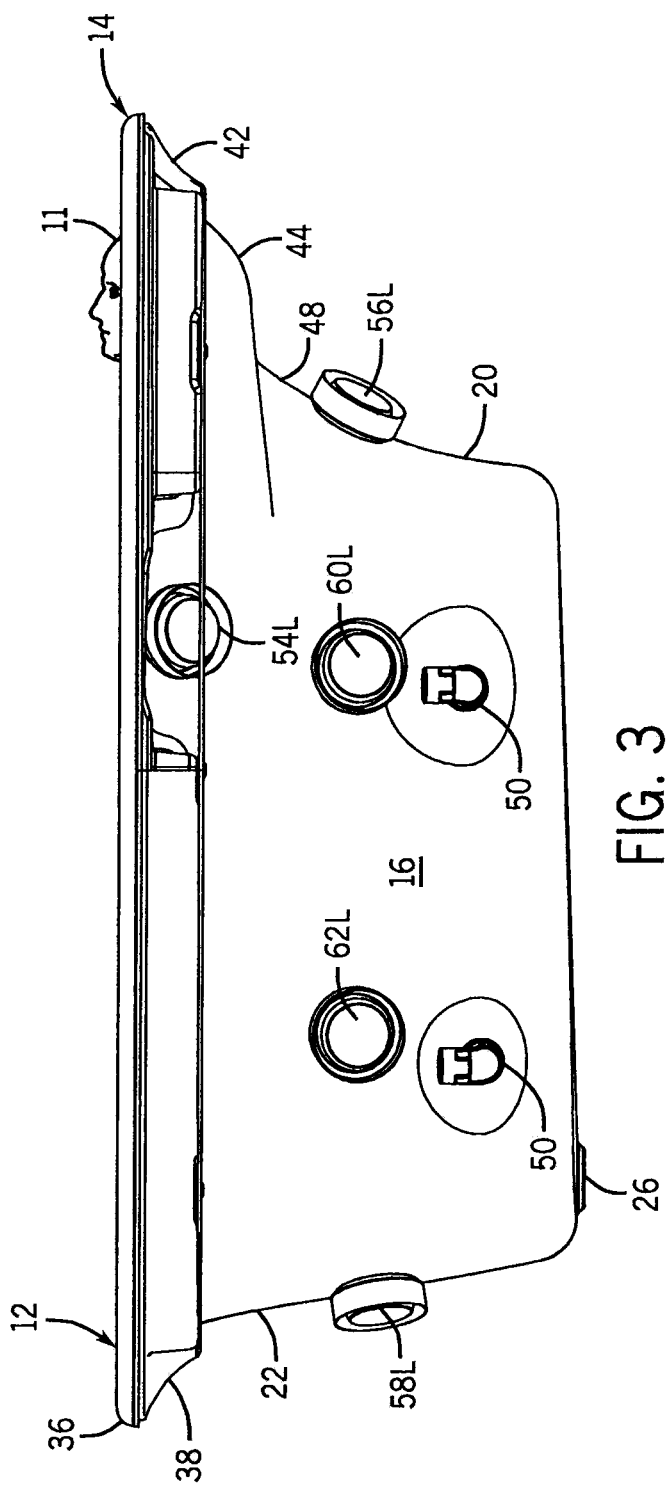
FIG. 3 is a left side elevation view thereof.
Figure 4:
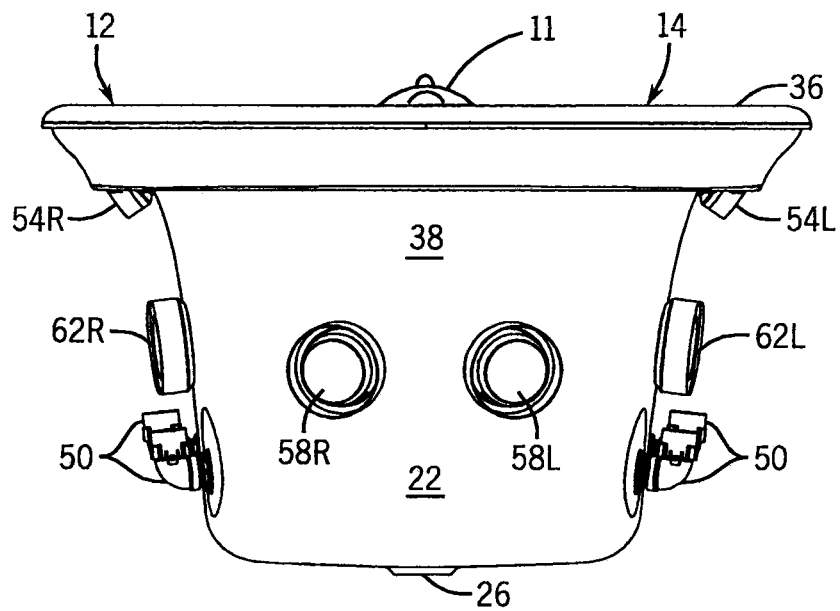
FIG. 4 is a foot end elevation view thereof.
Figure 5:
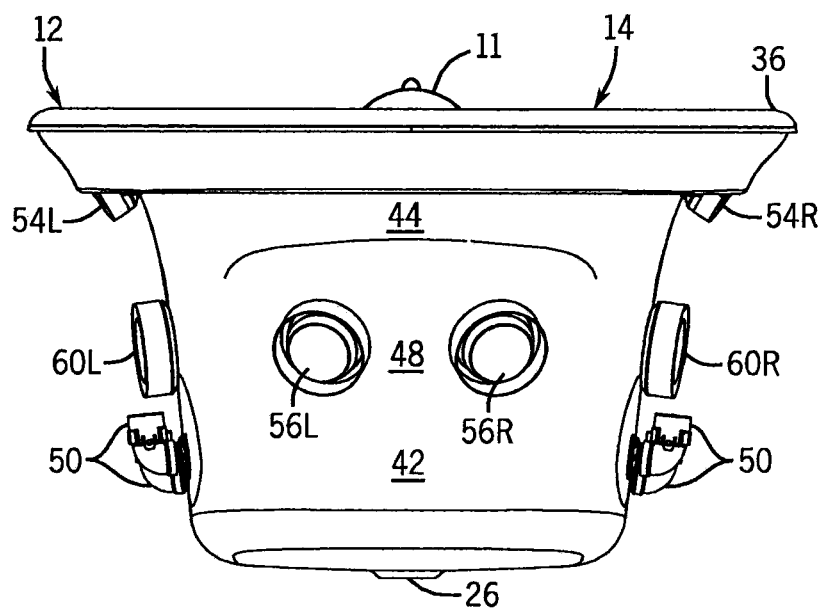
FIG. 5 is a head end elevation view thereof.
Figure 6A:
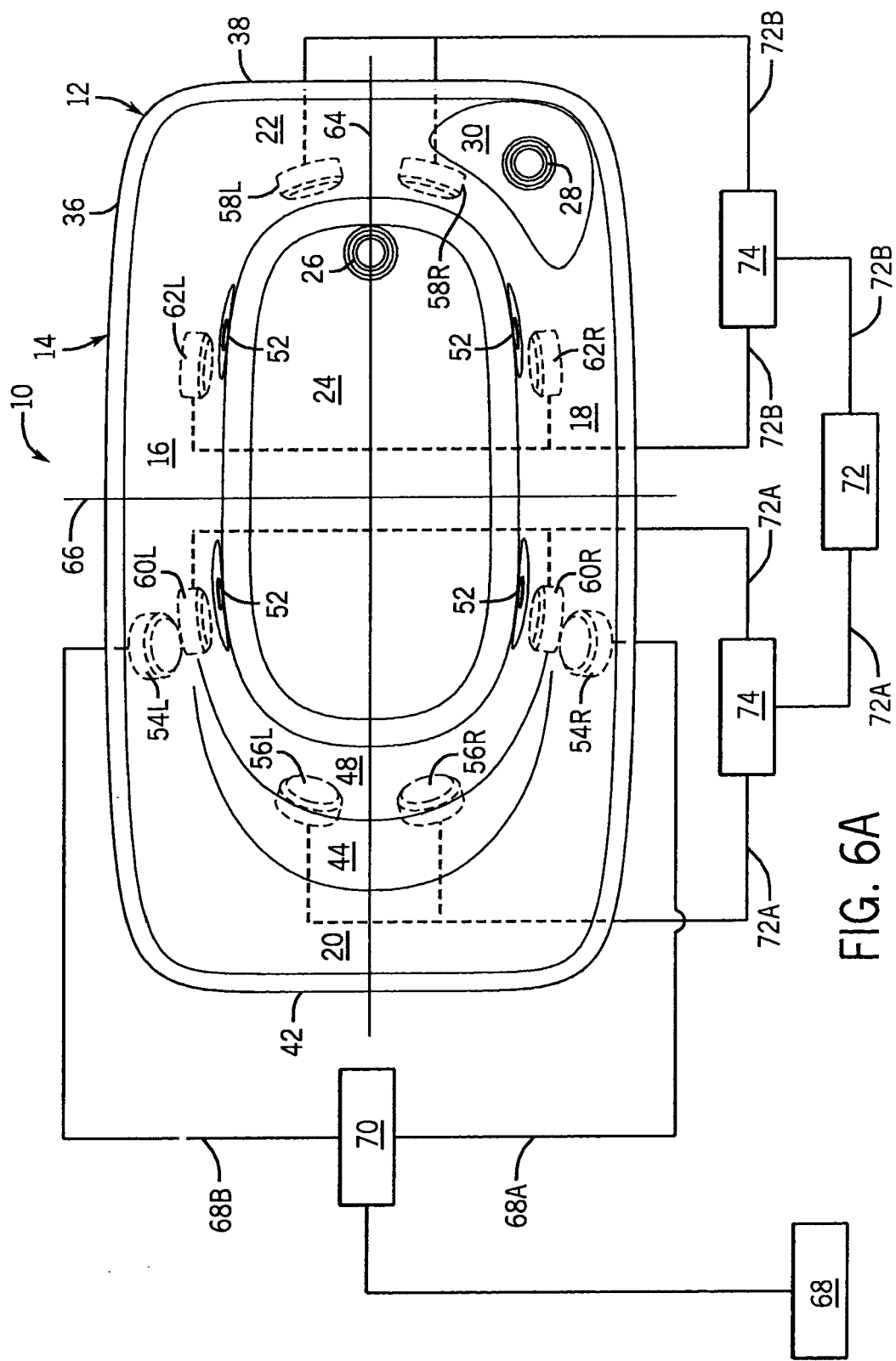
FIG. 6A is a schematic showing an exemplary wiring layout of the system of FIG. 1.
Figure 6B:
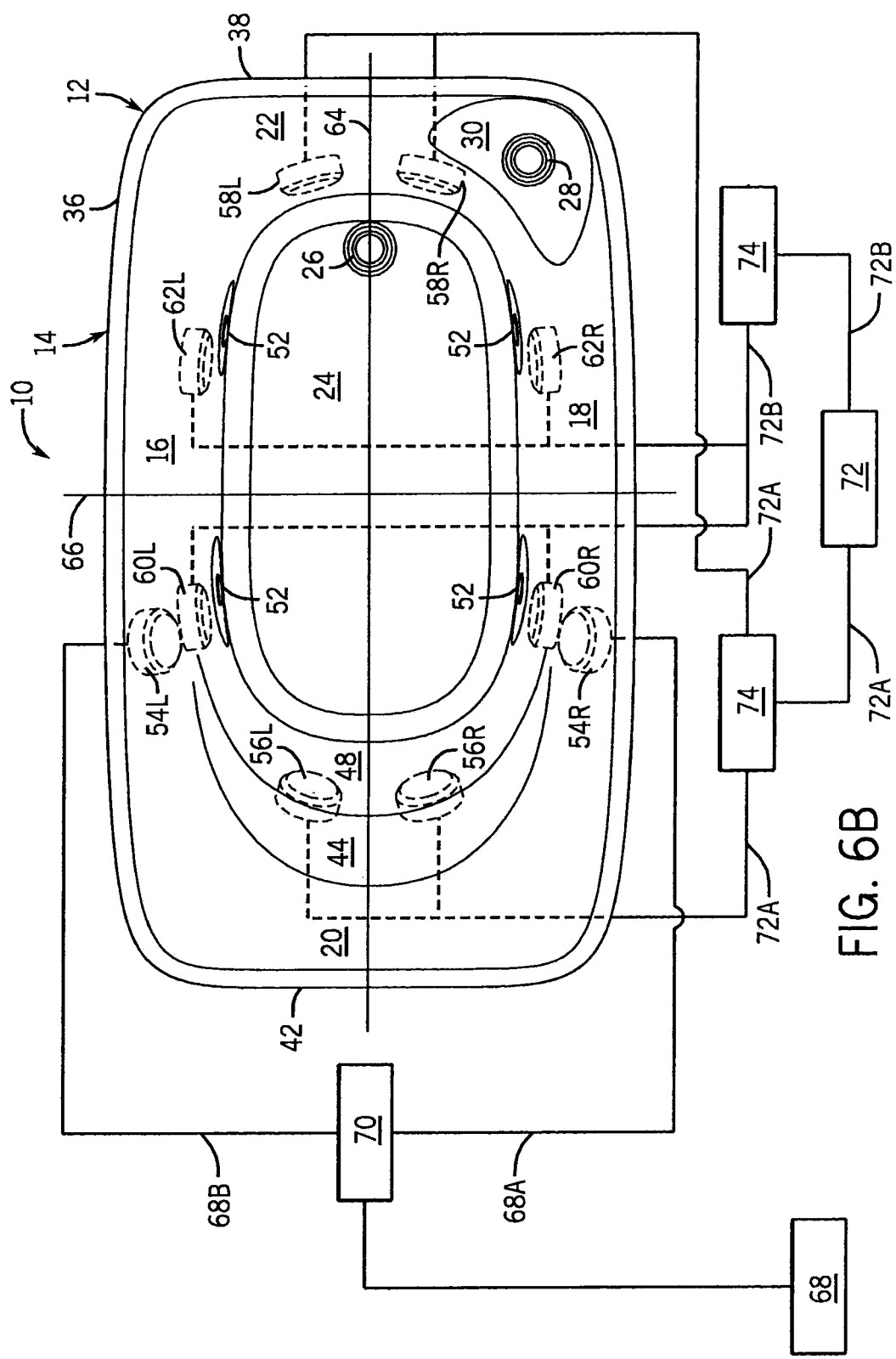
FIG. 6B is a schematic showing another exemplary wiring layout.

With specific reference to FIGS. 2, 6A, and 6B, the transducers are divided between two groups: (1) auditory transducers that vibrate the shell 14 to effect the auditory experience and (2) vibratory transducers that vibrate the shell 14 to effect the vibratory experience. The auditory transducers include a right audile transducer 54R and a left audile transducer 54L (collectively the "audile transducers 54R, 54L"). The vibratory transducers include a right head end vibratile transducer 56R, a left head end vibratile transducer 56L, a right foot end vibratile transducer 58R, a left foot end vibratile transducer 58L, a right side head end vibratile transducer 60R, a left side head end vibratile transducer 60L, a right side foot end vibratile transducer 62R, and a left side foot end vibratile transducer 62L (collectively the "vibratile transducers 56R, 56L, 58R, 58L, 60R, 60L, 62R, 62L").

The example embodiment described uses a total of two auditory transducers 54R, 54L and eight vibratory transducers 56R, 56L, 58R, 58L, 60R, 60L, 62R, 62L; however, any number of auditory and vibratory transducers may be incorporated in accordance with the present invention. In addition, while the preferred transducer placement and quantity is shown, the placement of the transducers may be altered, and in fact, are preferably adjusted to accommodate a user's interaction with each particular fixture 12 (e.g., bathtub) to maximize the auditory and vibratory experiences. Given the shell 14 shown in the example embodiment, the transducers are preferably placed in the relative arrangement as shown to maximize the transmission of the wave characteristics effected by the auditory and vibratory experiences. For example, the audile transducers 54R, 54L are oriented as shown to direct the auditory experience toward the bather 11 to effect the desired aural stimulus.

Each transducer is mounted in a location to produce either, or both, a localized experience or an overall experience. The vibratile transducers 56R, 56L, 58R, 58L, 60R, 60L, 62R, 62L are preferably mounted to the shell 14 below the waterline 32 such that the corresponding vibrations produce a tactile, vibratory experience that propagates through the water.

As an example of a localized vibratory experience, the right head end vibratile transducer 60R and the left head end vibratile transducer 60L are secured to the shell 14 proximate the backrest portion 48 such that energy produced by the right head end vibratile transducer 60R and the left head end vibratile transducer 60L vibrate the shell 14 proximate the backrest portion 48 and produce a corresponding energy wave in the liquid medium that propagates from the shell 14 to the bather 11. The vibratory experience is perceived tactilely by the bather 11 as a controlled, directed vibration of the back, chest, and all internal biological structures proximate the right head end vibratile transducer 60R and the left head end vibratile transducer 60L. Similar controlled, localized effects are produced by the remaining vibratile transducers 56R, 56L, 58R, 58L, 60R, 60L, 62R, 62L located at desired positions around the shell 14.

Figure 7A:
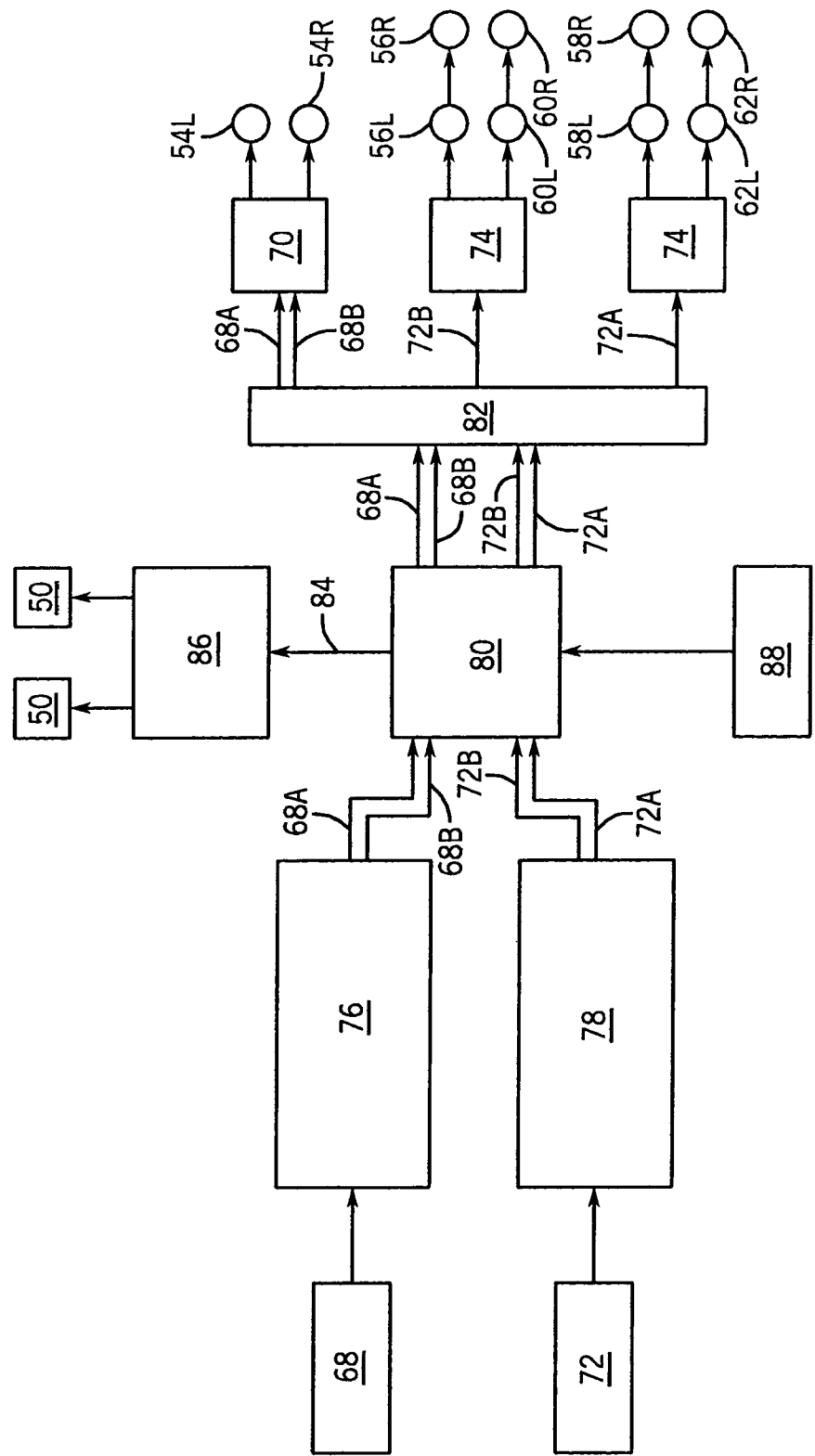
FIG. 7A is a schematic showing an exemplary signal distribution of the system of FIG. 1.

The vibratile transducers 56R, 56L, 58R, 58L, 60R, 60L, 62R, 62L can also be controlled in concert to produce an overall vibratory experience that propagates to multiple regions or zones within the shell 14 or along a predetermined path. In one embodiment, as shown in FIGS. 6A and 7A, the right foot end vibratile transducer 58R and the left foot end vibratile transducer 58L can be controlled in concert with the right head end vibratile transducer 56R and the left head end vibratile transducer 56L to produce a controlled, combined vibratory experience that propagates back and forth between the feet and head of the bather 11. This provides a vibratory experience having a tactile stimulus that propagates through the bather 11 between the head and feet of the bather 11.

Figure 7B:
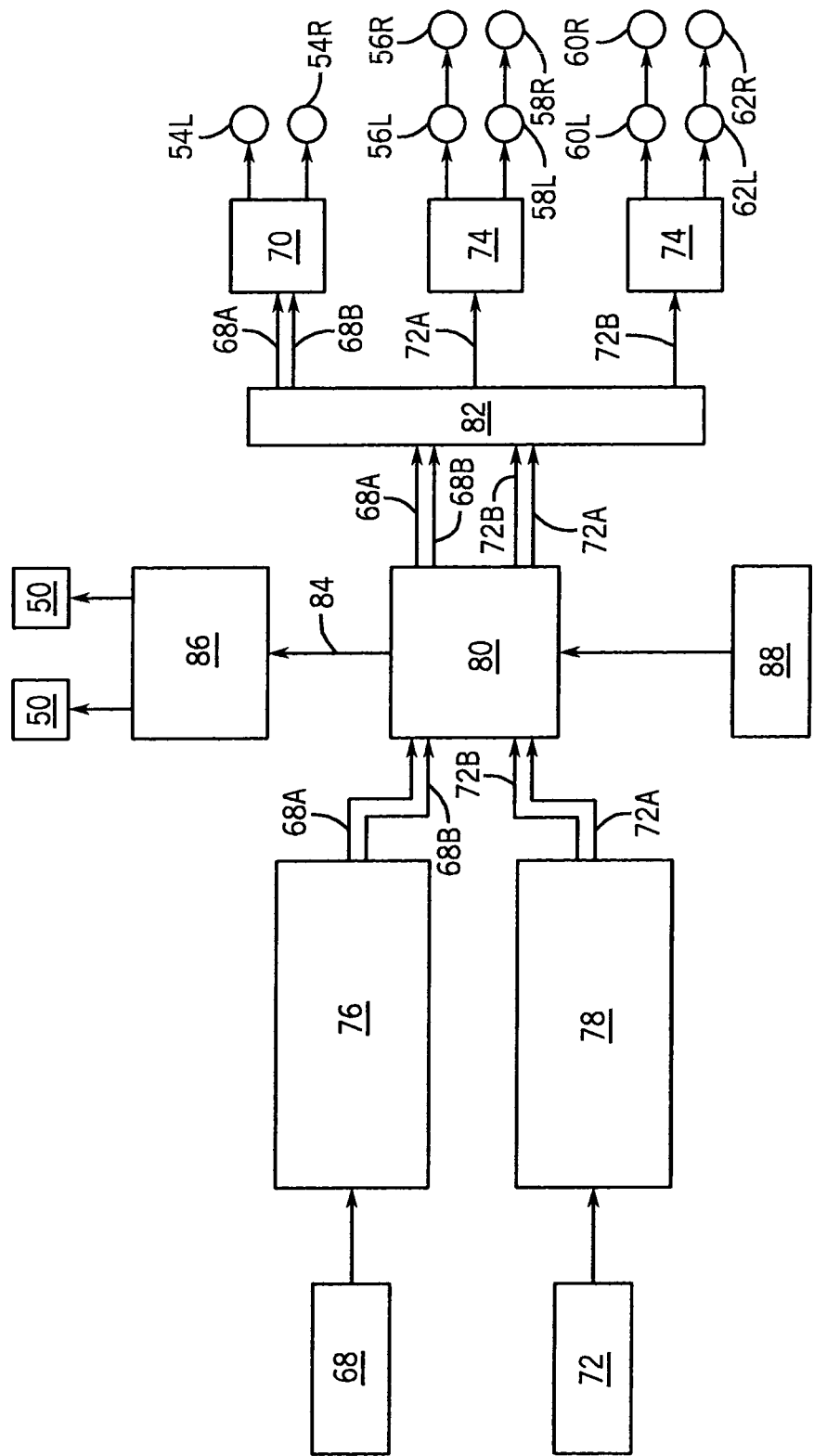
FIG. 7B is a schematic showing another exemplary signal distribution.

In another embodiment, as shown in FIGS. 6B and 7B, the four centralized vibratile transducers, including the right side head end vibratile transducer 60R, left side head end vibratile transducer 60L, right side foot end vibratile transducer 62R, and left side foot end vibratile transducer 62L, are controlled in concert and discretely from the four vibratile transducers proximate the head end 42 and the foot end 38, including the right head end vibratile transducer 56R, left head end vibratile transducer 56L, right foot end vibratile transducer 58R, and left foot end vibratile transducer 58L. This configuration can effect a tactile stimulus that selectively directs the vibratory experience between the core and the head/feet of the bather 11. As one skilled in the art will appreciate, a multitude of transducer coupling configurations are available to effect a vibratory experience to a bather 11.

The audile transducers 54R, 54L are preferably mounted proximate the rim 36, essentially above the waterline 32, and biased toward the head end 42 of the shell 14. This places the audile transducers 54R, 54L closer to the head of the bather 11 and essentially above the water in the shell 14. As a result, the placement enhances the auditory experience created by the audile transducers 54R, 54L as the shell 14 vibrates the surrounding air to effect the aural stimulus. Again, the design of the shell 14, specifically the portion proximate the rim 36, has been tuned to enhance the wave characteristics of the auditory experience to maximize the aural stimulus.

In the example embodiment, the right head end vibratile transducer 56R, left head end vibratile transducer 56L, right foot end vibratile transducer 58R, and left foot end vibratile transducer 58L are generally spaced apart along a longitudinal axis 64. Similarly, the right side head end vibratile transducer 60R, left side head end vibratile transducer 60L, right side foot end vibratile transducer 62R, and left side foot end vibratile transducer 62L are generally spaced apart along a transverse axis 66. The right audile transducer 54R and the left audile transducer 54L are also oriented generally along the transverse axis 66.

This general orthogonal arrangement of the transducers 54R, 54L, 56R, 56L, 58R, 58L, 60R, 60L, 62R, 62L allows the shell 14 to produce simultaneous auditory and vibratory experiences that are dependent in part on the relative spacing between and arrangement of the transducers. The auditory and vibratory experiences may include controlled application of the experiences, including, panning, stereophonic imaging, focused vibrations, and the like, within or between the quadrants generally established by the longitudinal axis 64 and the transverse axis 66. Additionally, the aural and tactile stimuli of the auditory and vibratory experiences may be controlled, for example, in location, amplitude, frequency, duration, and interaction of the resulting auditory and/or vibratory experiences. The wave characteristics of the experiences can be manipulated to effect a multitude of experiences.

The transducers 54R, 54L, 56R, 56L, 58R, 58L, 60R, 60L, 62R, 62L are mounted to the shell 14 by any known means, including but not limited to adhesives and epoxies, which securely couple the transducers 54R, 54L, 56R, 56L, 58R, 58L, 60R, 60L, 62R, 62L to the shell 14 and create an energy coupling relationship between the shell 14 and the transducer. The preferred coupling ensures an efficient transfer of energy from the transducer 54R, 54L, 56R, 56L, 58R, 58L, 60R, 60L, 62R, 62L to the shell 14 such that the auditory experience and the vibratory experience are sufficiently produced by the shell to effect the desired aural and tactile stimuli.

With specific reference to FIG. 6A, a simplified exemplary general signal stream and wiring schematic of the vibroacoustic bathing system 12 is shown. For clarity, the audile components will be described separately from the vibratile components. Signal generation and processing will be described in greater detail with reference to FIG. 7A.

The auditory experience is a result of the audile signal 68 and its audile wave characteristics. The audile signal 68 contains the instructions (i.e., characteristics) for the audile transducers 54R, 54L to vibrate the shell 14 to produce the auditory experience that is effected as an aural stimulus. The audile signal 68 is routed through an audile amplifier 70 before driving the right audile transducer 54R and the left audile transducer 54L. The audile signal 68 preferably comprises a first audile channel 68A and a second audile channel 68B. The first audile channel 68A drives the right audile transducer 54R and the second audile channel 68B drives the left audile transducer 54L. The first audile channel 68A and the second audile channel 68B can carry a similar or distinct audile signal 68 to the respective audile transducer 54R, 54L depending on the desired auditory experience. For example, an aural panning effect along the transverse axis 66 can be accomplished by manipulating the audile wave characteristics, such as the frequency and/or amplitude, of the first audile channel 68A in concert with the second audile channel 68B.

While the audile signal 68 of the example embodiment is a two-channel signal, it is contemplated that any other type of signal is equally applicable to the current invention. For example, the audile signal 68 may be encoded such that information related to multiple channels (e.g., 4, 5, 7, etc.) may be decoded from the audile signal 68, amplified by one, or multiple, audile amplifiers 70, and connected to the appropriate transducers to produce the desired auditory experience.

The vibratory experience is a result of the vibratile signal 72 and its vibratile wave characteristics. The vibratile signal 72 contains the instructions (i.e., characteristics) for the vibratile transducers 56R, 56L, 58R, 58L, 60R, 60L, 62R, 62L to produce the vibratory experience that is effected by a tactile stimulus. In the example embodiment, the vibratile signal 72 is routed through a pair of vibratile amplifiers 74 before driving the vibratile transducers 56R, 56L, 58R, 58L, 60R, 60L, 62R, 62L. The vibratile signal 72 preferably comprises a first vibratile channel 72A and a second vibratile channel 72B.

In one example embodiment shown in FIGS. 6A and 7A, the first vibratile channel 72A drives the right head end vibratile transducer 56R, the left head end vibratile transducer 56L, the right side head end vibratile transducer 60R, and the left side head end vibratile transducer 60L (collectively the "head end vibratile transducers 56R, 56L, 60R, 60L"). The second vibratile channel 72B drives the right foot end vibratile transducer 58R, the left foot end vibratile transducer 58L, the right side foot end vibratile transducer 62R, and the left side foot end vibratile transducer 62L (collectively the "foot end vibratile transducers 58R, 58L, 62R, 62L").

As best shown in FIG. 6A, the right head end vibratile transducer 56R and the left head end vibratile transducer 56L are connected in series and the right side head end vibratile transducer 60R and the left side head end vibratile transducer 60L are also connected in series. However, the head end vibratile transducers 56R, 56L, 60R, 60L are driven by the first vibratile channel 72A. A similar coupling is shown with respect to the foot end vibratile transducers 58R, 58L, 62R, 62L that are driven by the second vibratile channel 72B. The configuration shown allows for the first vibratile channel 72A and second vibratile channel 72B to drive the respective head end vibratile transducers 56R, 56L, 60R, 60L and foot end vibratile transducers 58R, 58L, 62R, 62L with two distinct vibratile signals 72. As a result, a controlled vibratory experience can be effected by varying the vibratile wave characteristics (e.g., intensity, duration, frequency, and the like), in relation to the head end vibratile transducers 56R, 56L, 60R, 60L relative to the foot end vibratile transducers 58R, 58L, 62R, 62L. Thus the tactile stimulus of the vibratory experience can be manipulated in position, intensity, duration, and the like.

Another example embodiment is shown in FIGS. 6B and 7B in which the first vibratile channel 72A drives the right head end vibratile transducer 56R, the left head end vibratile transducer 56L, the right foot end vibratile transducer 58R, and the left foot end vibratile transducer 58L (collectively the "end vibratile transducers 56R, 56L, 58R, 58L"). The second vibratile channel 72B drives the right side foot end vibratile transducer 62R, the left side foot end vibratile transducer 62L, the right side head end vibratile transducer 60R, and the left side head end vibratile transducer 60L (collectively the "core vibratile transducers 60R, 60L. 62R, 62L").

As best shown in FIG. 6B, the end vibratile transducers 56R, 56L, 58R, 58L are driven by the first vibratile channel 72A. Similarly, the core vibratile transducers 60R, 60L, 62R, 62L are driven by the second vibratile channel 72B. This transducer configuration shown allows for the first vibratile channel 72A and second vibratile channel 72B to drive the respective end vibratile transducers 56R, 56L, 58R, 58L and core vibratile transducers 60R, 60L, 62R, 62L with two distinct vibratile signals 72. As a result, a controlled vibratory experience can be effected by varying the vibratile wave characteristics (e.g., intensity, duration, frequency, and the like), in relation to the end vibratile transducers 56R, 56L, 58R, 58L relative to the core vibratile transducers 60R, 60L, 62R, 62L. Thus the tactile stimulus of the vibratory experience can be manipulated in position, intensity, duration, and the like.

As with the first audile channel 68A and the second audile channel 68B, the characteristics of the first vibratile channel 72A and the second vibratile channel 72B can be varied to create general or localized vibratory experiences, such as panning from the foot end 38 to the head end 42. As with the audile transducers 54R, 54L, the vibratile transducers 56R, 56L, 58R, 58L, 60R, 60L, 62R, 62L each may be driven by a separate and discrete vibratile signal 72 that may be encoded in the vibratile signal 72. Further, each vibratile transducer 56R, 56L, 58R, 58L, 60R, 60L, 62R, 62L can be driven by a discrete vibratile amplifier 74, thus allowing independent control, depending upon the application requirements.

In the example embodiment, and with specific reference to FIG. 7A, the auditory experience and the vibratory experience are encoded into the audile signal 68 and the vibratile signal 72, respectively. Alternatively, the audile signal 68 and the vibratile signal 72 may be encoded into a single source signal and decoded therefrom as necessary. Preferably, the audile signal 68 and vibratile signal 72 are encoded in Movie Picture Experts Group Layer-3 format ("MP3 format"), but may be encoded with any other codec or presented in raw format (e.g., Waveform ("WAV"), Advanced Audio Coding ("AAC"), Dolby Digital, and the like).

The audile signal 68 and vibratile signal 72 are preferably extracted from separate media devices (not shown) such as a Secure Digital ("SD") card, miniSD, CompactFlash, flash drive, and the like. Alternatively, the audile signal 68 and vibratile signal 72 may be stored in a built-in storage media (e.g., a hard drive) or on optical media (e.g., compact disc ("CD"), digital versatile disk ("DVD"), Blue-ray Disk ("BD"), and the like). Thus, the audile signal 68 and the vibratile signal 72 may be extracted from a single media device and from a single stream.

In the example embodiment, the audile signal 68 is directed to an audile decoder 76 where it is decoded from MP3 format into a streaming audile signal 68 preferably comprising the first audile channel 68A and the second audile channel 68B. Similarly, the vibratile signal 72 is routed to a vibratile decoder 78 where it is decoded from the preferred MP3 format to a streaming vibratile signal 72 comprising the first vibratile channel 72A and the second vibratile channel 72B. The audile decoder 76 and the vibratile decoder 78 may be similar to the SCF5250 Integrated ColdFire Microprocessor produced by Freescale Semiconductor. Alternatively, a single decoder may decode the audile signal 68 and the vibratile signal 72.

The output from the audile decoder 76 (i.e., the first audile channel 68A and the second audile channel 68B) and the vibratile decoder 78 (i.e., the first vibratile channel 72A and the second vibratile channel 72B) are directed into a controller 80. In the example embodiment, the controller 80 can be any number of complex programmable logic devices commonly available. The controller 80 routes the first audile channel 68A, second audile channel 68B, first vibratile channel 72A, and second vibratile channel 72B to the appropriate input on a signal processor 82 (described below). It should be appreciated that the controller 80 may integrate one, several, or all of the functions and features of the decoders 76, 78, signal processor 82, amplifiers 70, 74, chromotherapy controller 86, and any other component used in the vibroacoustic bathing system 12. The functions and features of the various components of the example embodiment have been separated for ease of explanation.

The controller 80 provides at least one chromo signal 84 to a chromotherapy controller 86. The chromotherapy controller 86 manipulates a series of chromotherapy devices 50 (e.g., LEDs) in response to the chromo signal 84 received from the controller 80. A variety of color combinations, intensities, patterns, and the like are directed into the shell 14 via the chromotherapy controller 86 and integrated chromotherapy devices 50.

The signal processor 82 of the example embodiment manipulates and conditions the audile signal 68 and the vibratile signal 72. The signal processor 82 may be used to adjust the vibratile wave characteristics or the audile wave characteristics, such as the frequency and amplitude of the first audile channel 68A, second audile channel 68B, first vibratile channel 72A, second vibratile channel 72B, and any other input signal. The signal processor 82 may be similar to the TAS5508A made by Texas Instruments. Additionally, the signal processor may include a series of amplifiers; however, the example embodiment shown in FIGS. 6A and 7A incorporates an audile amplifier 70 to drive the audile transducers 54R, 54L and a pair of vibratile amplifiers 74, one to drive the head end vibratile transducers 56R, 56L, 60R, 60L and one to drive the foot end vibratile transducers 58R, 58L, 62R, 62L. One skilled in the art will appreciate the variety of amplifier configurations and combinations available to power the vibroacoustic bathing system 12. For example, a circuit board may include a series of chips that include a pair of amplifiers each receiving an input signal. The amplifiers may be electrically coupled in a variety of ways to better distribute thermal energy during operation, such as by electrically coupling one or more chips.

With continued reference to FIG. 7A, the configuration of the audile transducers 54R, 54L and configuration of the head end vibratile transducers 56R, 56L, 60R, 60L and the foot end vibratile transducers 58R, 58L, 62R, 62L is illustrated. This example configuration allows the audile signal 68 to be discretely distributed between the audile transducers 54R, 54L to achieve the desired auditory experience. With reference to FIG. 7B, the configuration of the end vibratile transducers 56R, 56L, 58R, 58L and core vibratile transducers 60R, 60L, 62R, 62L is illustrated. Additionally, the vibratile signal 72 can be manipulated to be distributed between the vibratile transducers 56R, 56L, 58R, 58L, 60R, 60L, 62R, 62L in a variety of ways to achieve the desired vibratory experience.

As described above, each transducer 54R, 54L, 56R, 56L, 58R, 58L, 60R, 60L, 62R, 62L may be independently controlled. For example, the controller 80 may output two distinct audile signals 68 and eight distinct vibratile signals 72, allowing independent control of each transducer 54R, 54L, 56R, 56L, 58R, 58L, 60R, 60L, 62R, 62L. For instance, a specific tactile stimulus can be produced by a specific vibratile transducer 56R, 56L, 58R, 58L, 60R, 60L, 62R, 62L by sending a discrete vibratile signal 72 from the controller 80 through the signal processor 82 and to the desired vibratile transducer 56R, 56L, 58R, 58L, 60R, 60L, 62R, 62L.

The controller 80 of the example embodiment also includes an auxiliary input 88. The controller 80 receives the auxiliary input 88 and routes the input to the desired audile transducers 54R, 54L and vibratile transducers 56R, 56L, 58R, 58L, 60R, 60L, 62R, 62L. The signal may be sent to one or all of the transducers as determined by the bather 11 via a user interface (not shown) or by the controller 80 in accordance with preprogrammed logic. For example, the controller 80 may be programmed to filter the auxiliary input 88 to direct lower frequencies (e.g., below approximately 250 hertz) to the vibratile transducers 56R, 56L, 58R, 58L, 60R, 60L, 62R, 62L and higher frequencies (e.g., above approximately 250 hertz) to the audile transducers 54R, 54L. Alternatively, the controller 80 may be programmed to extract the pulsating signals (i.e., the "beat") from the auxiliary input 88 and direct those signals to the vibratile transducers 56R, 56L, 58R, 58L, 60R, 60L, 62R, 62L. The balance of the auxiliary input 88 would then be directed to the audile transducers 54R, 54L. The auxiliary input 88 may be obtained from a variety of auxiliary devices (not shown) including a computer, a television, a digital media player, and the like.

Turning to FIGS. 8A-8F, simplified waveforms (whereat the Y-axis is generally representative of relative amplitude and the X-axis is generally representative of a temporal continuum) illustrating example audile signals 68 and vibratile signals 72 that are used to produce desired auditory and vibratory experiences are shown. The audile signals 68 and vibratile signals 72 illustrated are merely example waveforms that can be used to produce a desired aural stimulus and tactile stimulus by vibrating the shell 14. The vibratory experience and the auditory experience have at least one distinct wave characteristic as compared to the other experience. The characteristic may be related to frequency, amplitude, tone, duration, and any other wave characteristic and are preferably tuned to the shell 14. Additionally, it is of note that the vibratory experience and the auditory experience are preferably produced simultaneously by the shell 14 to effect the tactile and aural stimuli essentially simultaneously. Therefore, the transducers simultaneously drive the shell 14 to produce the desired experiences.

Figure 8A:
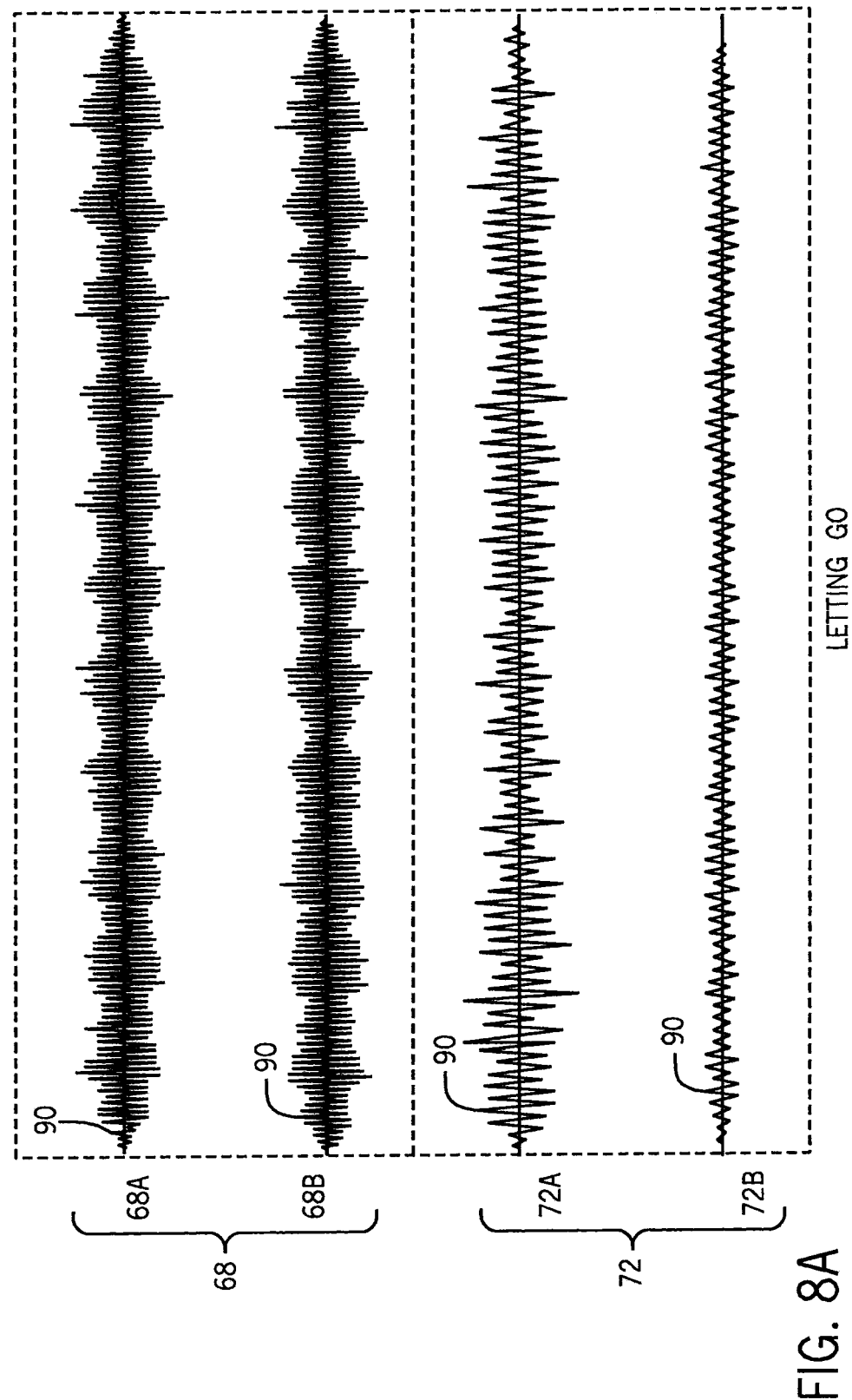
FIG. 8A is a simplified waveform useable with the system of FIG. 1 to establish a universal pulse.

With reference to FIG. 8A, the "letting go" waveforms 90 are designed to create an auditory experience and a vibratory experience that synchronize certain biological metrics (e.g., breathing rate, heart rate, and the like) of the bather 11 with a universal pulse established by the "letting go" waveforms 90. The auditory experience is imparted by the audile signal 68 that is directed via the first audile channel 68A and the second audile channel 68B to the right audile transducer 54R and the left audile transducer 54L, respectively. The auditory experience is then effected to the bather 11 as the shell 14 vibrates the surrounding air as an aural stimulus.

Similarly, in the embodiment shown in FIG. 6A, the vibratory experience is imparted by the vibratile signal 72 that is directed via the first vibratile channel 72A to the head end vibratile transducers 56R, 56L, 60R, 60L, and the second vibratile channel 72B to the foot end vibratile transducers 58R, 58L, 62R, 62L. In the alternative embodiment shown in FIG. 6B, the vibratory experience is imparted by the vibratile signal 72 that is directed via the first vibratile channel 72A to the end vibratile transducers 56R, 56L, 58R, 58L, and the second vibratile channel 72B to the core vibratile transducers 60R, 60L, 62R, 62L. The vibrations imparted to the shell 14 by the audile transducers 54R, 54L and vibratile transducers 56R, 56L, 58R, 58L, 60R, 60L, 62R, 62L establish a pulse that affects the bather 11 by entraining the subconscious breathing pattern to the repeating crescendos and decrescendos of the letting go waveforms 90. As previously noted, the shell 14 vibrates the water to propagate the vibratory experience; the vibratory experience is ultimately effected as a tactile stimulus. The vibratory experience effected by the "letting go" waveform is one example of a biorhythmic panning.

Figure 8B:
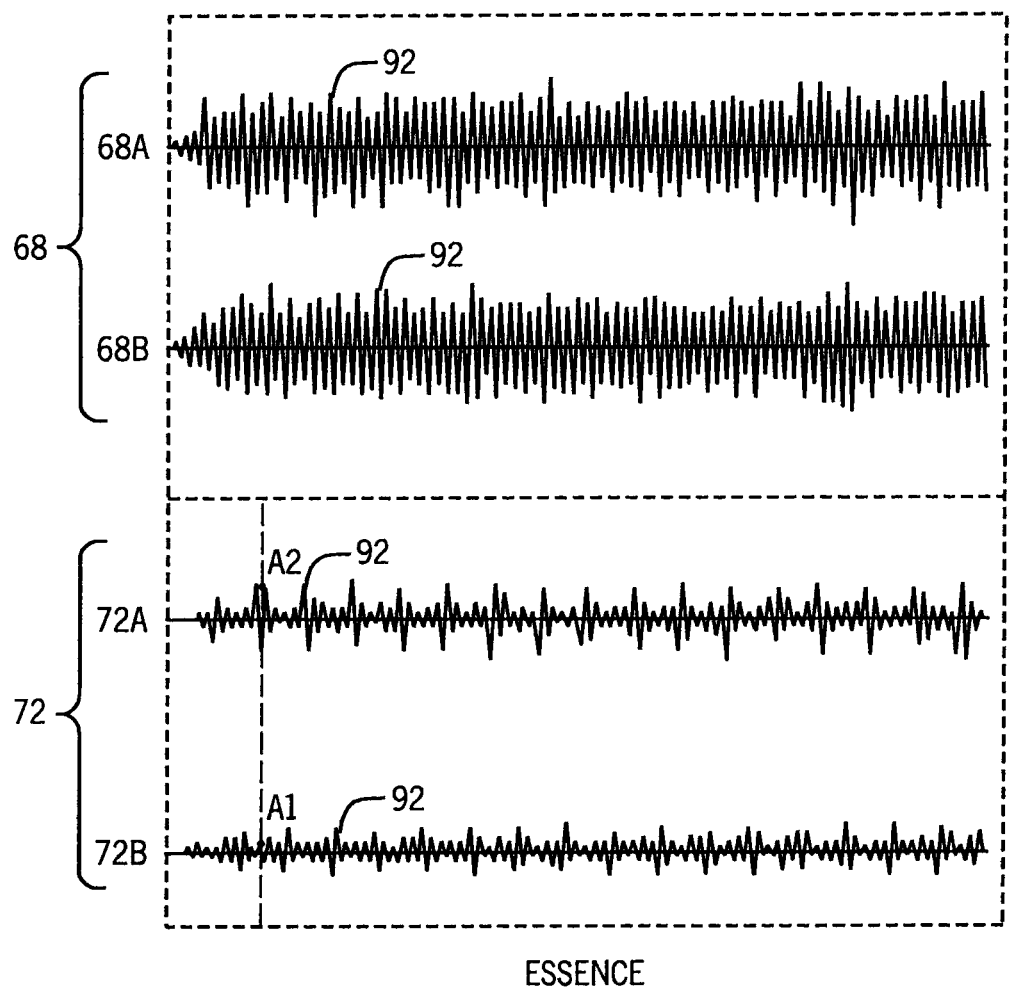
FIG. 8B is another simplified waveform useable with the system of FIG. 1 to establish a sweeping vibration.

Turning to FIG. 8B, the "essence" waveforms 92 are designed to create an auditory experience and a vibratory experience that again entrains the natural rhythms of the bather 11 to the pulse of the essence waveforms 92. In the embodiment shown in FIG. 6A, the essence waveforms 92 create a vibratory experience in which vibrations sweep from the foot end 38 of the shell 14 to the head end 42 of the shell 14, and then from the head end 42 to the foot end 38. Alternatively, the embodiment shown in FIG. 6B creates a vibratory experience in which vibrations pulse between the foot end 38 and head end 42, toward the transverse axis 66, and back toward the foot end 38 and head end 42. Looking at the vibratile signal 72, the peak amplitude A1 of the first vibratile channel 72A is temporally offset from the peak amplitude A2 of the second vibratile channel 72B, thus creating a sweeping vibratory experience as the shell 14 vibrates.

Figure 8C:
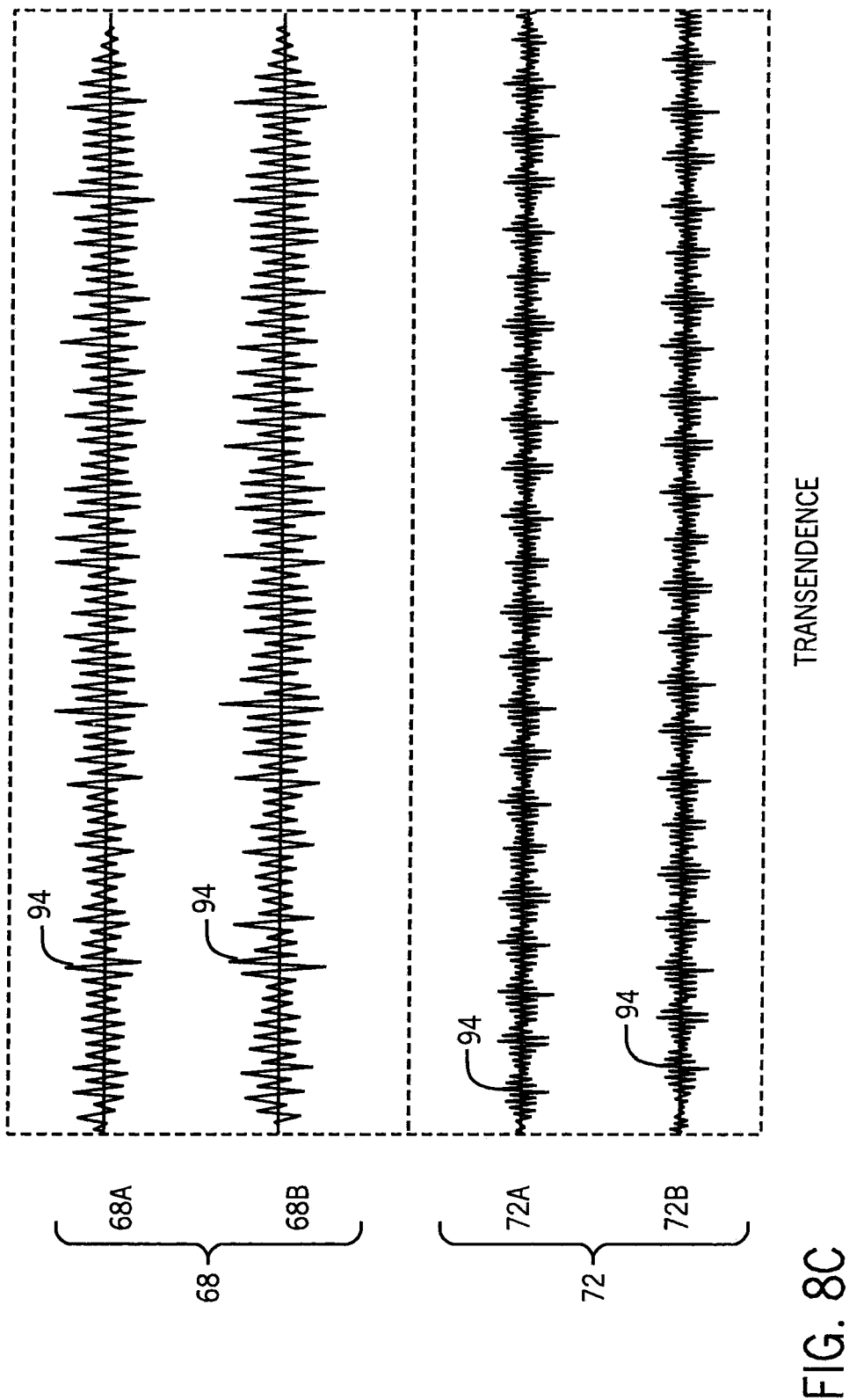
FIG. 8C is a further simplified waveform useable with the system of FIG. 1 to establish a periodic vibration.

With reference to the "transcendence" waveforms 94 shown in FIG. 8C, an additional exemplary set of auditory and vibratory experiences are described. The transcendence waveforms 94 establish a walking pulse having a vibratile signal 72 establishing a periodic vibratory experience that peaks repetitively approximately one second apart. Specifically, the first vibratile channel 72A is offset from the second vibratile channel 72B such that a distinctive vibratory experience is produced alternately proximate the head end 42 of the shell 14 and the foot end 38 of the shell 14, in the embodiment shown in FIG. 6A, and between the foot end 38/head end 42 and the transverse axis 66 in the embodiment shown in FIG. 6B, thereby establishing a rhythmic vibration of the shell 14.

Figure 8D:
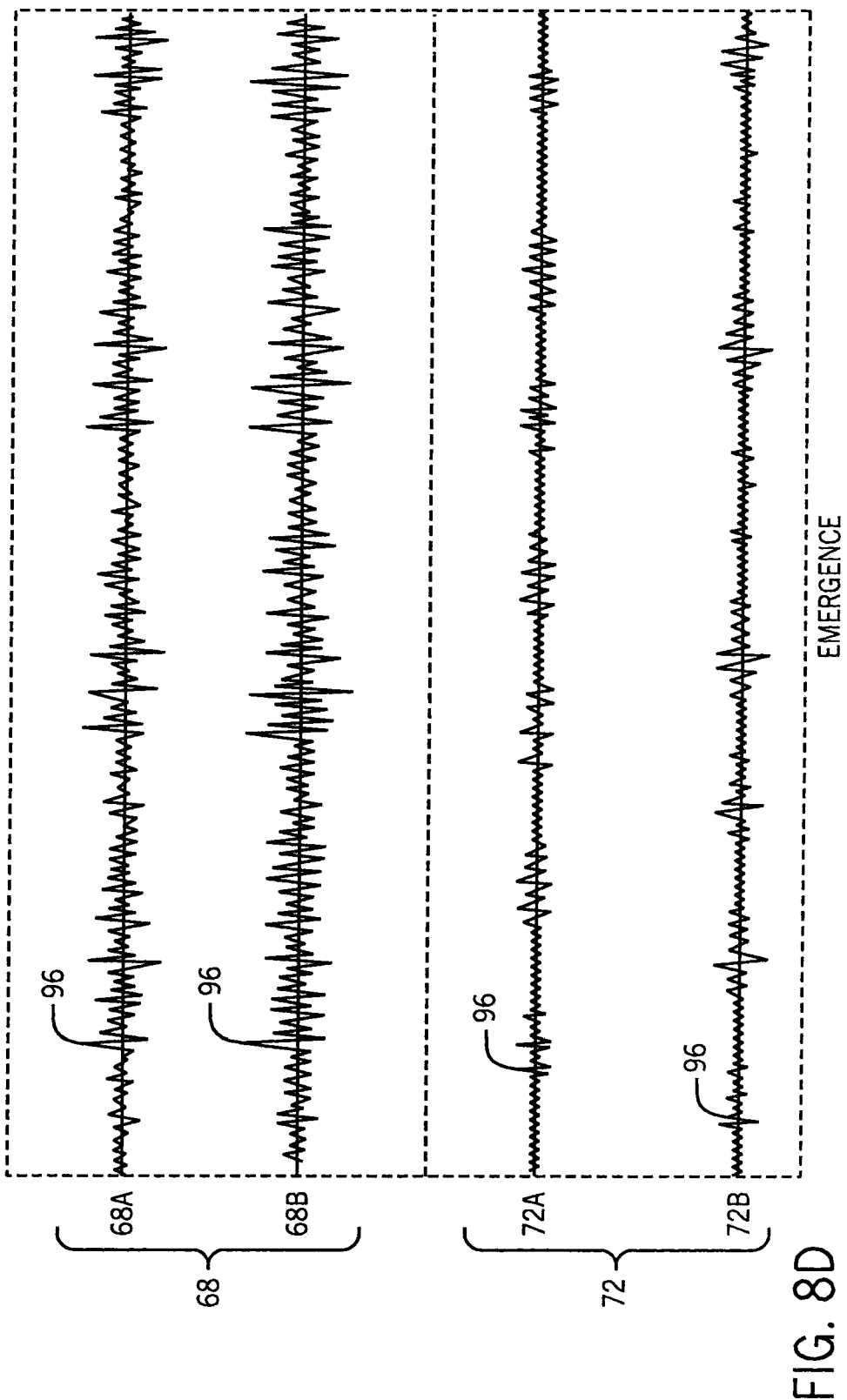
FIG. 8D is yet another simplified waveform useable with the system of FIG. 1 to establish a predominate auditory experience.

Turning to FIG. 8D, the "emergence" waveforms 96 are depicted and establish the auditory experience and the vibratory experience. The average amplitude of the audile signal 68 is notably greater than the vibratile signal 72 average amplitude. Thus, the perceived influence of the auditory experience effected via aural stimulus is greater than the vibratory experiences effected via tactile stimulus. As a result, the emergence waveforms 96 cause the bather to focus on the auditory experience more than the accompanying vibratory experience.

Figure 8E:
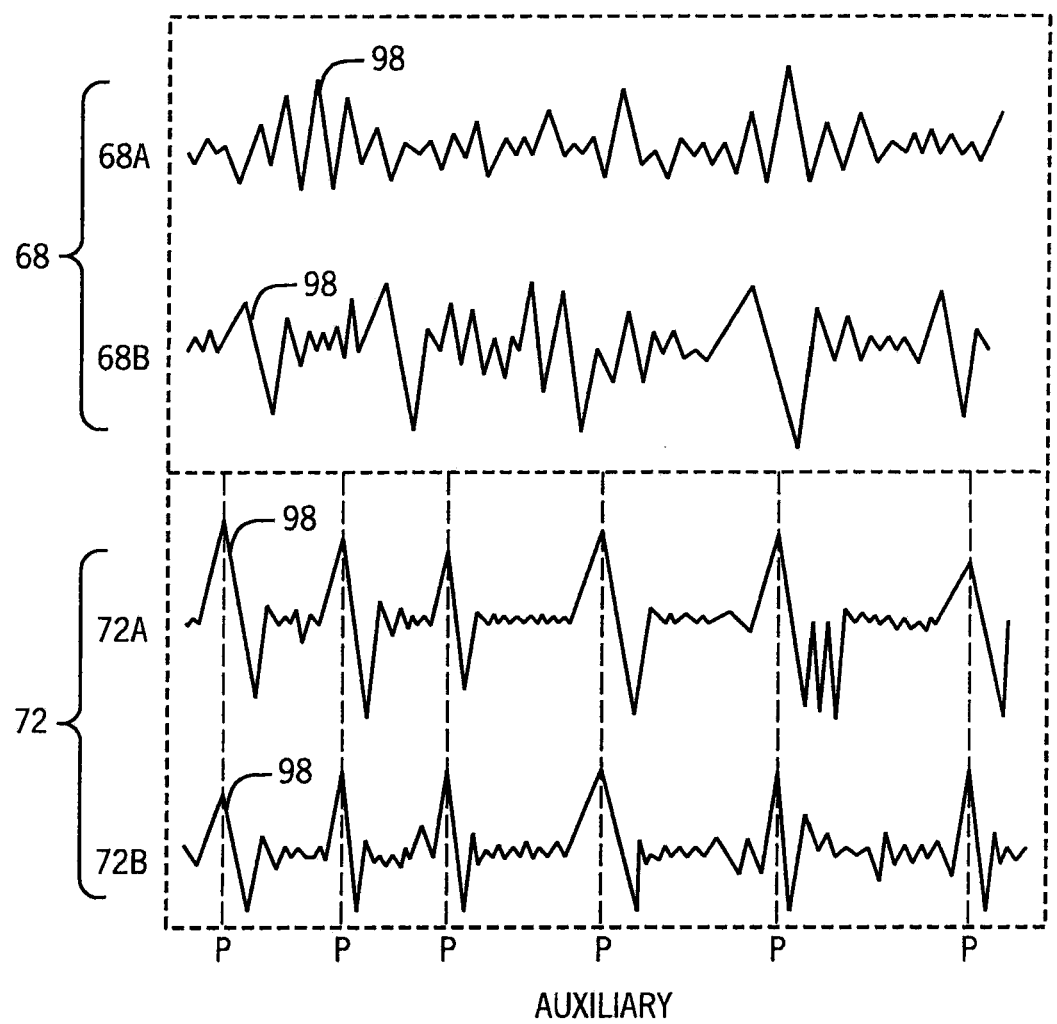
FIG. 8E is an example auxiliary waveform useable with the system of FIG. 1 to establish a vibratory experience and an auditory experience from an auxiliary input.

The "auxiliary" waveforms 98 are illustrated in FIG. 8E. The auxiliary waveforms 98 are indicative of the audile signal 68 and vibratile signal 72 that may be produced and routed to the respective audile transducers 54R, 54L and vibratile transducers 56R, 56L, 58R, 58L, 60R, 60L, 62R, 62L via the auxiliary input 88. In the auxiliary waveforms 98 shown, no auxiliary input 88 manipulation is performed, however, as discussed above, the signal may be manipulated (e.g., conditioned, filtered, deconstructed, and the like) to achieve a relative pre-determined auditory and vibratory experience. For example, the vibratile signal 72 may be analyzed to extract a pulse P that is in turn filtered from the audile signal 68 and emphasized in the vibratile signal 72. Additionally, the audile wave characteristics and vibratile wave characteristics may be manipulated to better interact with the shell 14 (i.e., be dynamically tuned to the shell 14). Numerous additional signal manipulation and processing techniques are within the scope of the present invention and known to those in the art.

Figure 8F:
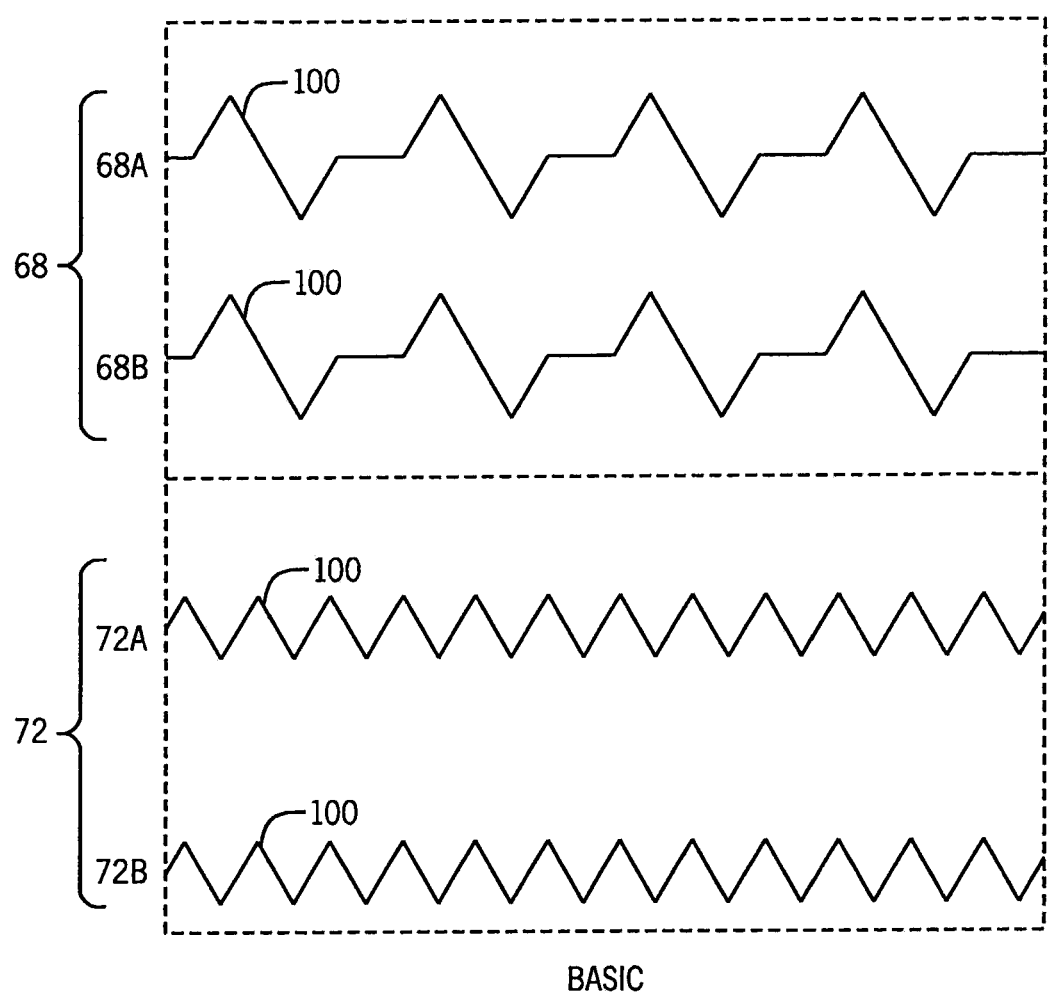
FIG. 8F is an example basic waveform useable with the system of FIG. 1 to establish a distinct vibratory experience.

In addition to the complex waveforms illustrated in FIGS. 8A-8E, "basic" waveforms 100, such as those shown in FIG. 8F, may be designed to impart an auditory experience and a vibratory experience more akin to a repetitive massage or drum beat. Many variations are contemplated and within the scope of the present invention.

As described above, the vibroacoustic bathing system 12 can be configured to create a variety of controlled auditory and vibratory experiences that are effected as a result of the shell 14 vibrating to produce both aural and tactile stimuli.

Preferred example embodiments of the present invention have been described in considerable detail. Many modifications and variations of the preferred example embodiments described will be apparent to a person of ordinary skill in the art. Therefore, the invention should not be limited to the example embodiments described.

INDUSTRIAL APPLICABILITY

The invention provides a vibroacoustic plumbing fixture for use in consumer bathing applications, specifically, a bathing system capable of producing controlled auditory and vibratory experiences.

We claim:

1. A vibroacoustic water system, comprising: a shell for containing water, the shell comprising a left side wall and a right side wall offset on opposite sides of a first axis, and a head wall and a foot wall offset on opposite sides of a second axis perpendicular to the first axis, wherein the first axis and the second axis define four quadrants, wherein the left side wall, the right side wall, the head wall, and the foot wall form a closed perimeter of the shell;
   a set of audile transducers mounted in energy transmitting relation to the shell, the set of audile transducers receiving an audile input signal having an audile wave characteristic and driving the shell to effect an aural stimulus;
   a set of at least four vibratile transducers mounted in energy transmitting relation to the shell and positioned below a waterline of water in the shell, wherein at least one of the vibratile transducers is arranged in each of the four quadrants and secured to each of the head wall, the foot wall, the left side wall, and the right side wall, the vibratile transducers receiving a vibratile input signal having a vibratile wave characteristic different from the audile wave characteristic and driving the shell to effect a tactile stimulus in the water which is different from the aural stimulus;
   the shell further comprising a head pocket formed on the head wall of the shell and above a backrest portion of the head wall, the head pocket extending substantially horizontally outside the closed perimeter, and curving upward and connecting to a rim of the shell; and
   a controller comprising preprogrammed logic that causes the controller to distribute the audile input signal between the set of audile transducers to achieve a desired auditory experience, and to distribute the vibratile input signal between the at least four vibratile transducers to achieve a desired vibratory experience, thereby creating a spatial center location for each of the aural and tactile stimuli, wherein the controller causes the spatial center of the tactile stimulus to move between each of the four quadrants along two dimensions of a plane defined by the first and second axes, wherein the controller causes the spatial centers of the aural stimulus and the tactile stimulus to move in coordination with each other so as to provide spatially-varying and coordinated vibratory and auditory experiences;
   wherein the controller is configured to receive an auxiliary input and to route the auxiliary input to the audile transducers and the vibratile transducers, wherein the controller is further configured to analyze the auxiliary input to extract pulsating signals forming a beat, and wherein the controller is further configured to cause the extracted pulsating signals to be provided to the vibratile transducers and filtered from the audile signal.

2. The system of claim 1, wherein the set of vibratile transducers comprises a first set of vibratile transducers located at a first side of the first axis, and a second set of vibratile transducers located at a second side of the first axis.

3. The system of claim 2, wherein the tactile stimulus is spatially directed to one or both sides of the first axis.

4. The system of claim 3, wherein the tactile stimulus pans between the first set of vibratile transducers and the second set of vibratile transducers across the first axis.

5. The system of claim 4, wherein the tactile stimulus pans in a biorhythmic pattern.

6. The system of claim 4, wherein the first axis extends along a long dimension of the shell.

7. The system of claim 2, wherein the audile input signal received by the set of audile transducers is multi-channel, and wherein the set of audile transducers is arranged such that at least one of the audile transducers is located to each side of the second axis.

8. The system of claim 7, wherein the aural stimulus is spatially directed to one or both sides of the second shell axis.

9. The system of claim 8, wherein the aural stimulus pans between at least two of the set of audile transducers across the second shell axis.

10. The system of claim 8, wherein the first shell axis extends along a long dimension of the shell and the second shell axis extends along a short dimension of the shell.

11. The system of claim 10, wherein each of the aural and tactile stimuli is directed spatially to one or more of the quadrants.

12. The system of claim 11, wherein the spatial center location of the tactile stimulus is coordinated with the spatial center location of the aural stimulus.

13. The system of claim 12, wherein the spatial centers of the aural and tactile stimuli are located in the same quadrant as each other.

14. The system of claim 12, wherein the spatial center of the aural stimulus moves in coordination with the spatial center of the tactile stimulus so as to provide a spatially varying aural and tactile experience.

15. The system of claim 1, wherein the plurality of transducers comprise at least eight vibratile transducers dedicated to the tactile stimulus and positioned below the waterline, wherein at least two of the vibratile transducers are arranged in each of the four quadrants and secured to each of the head wall, the foot wall, the left side wall, and the right side wall.

16. The system of claim 15, wherein each of the four quadrants comprises at least one of the vibratile transducers secured to one of the left side wall and the right side wall and at least one of the vibratile transducers secured to one of the head wall and the foot wall.

17. The system of claim 15, wherein the at least two vibratile transducers in each of the four quadrants are arranged symmetrically about the first axis with respect to another at least two vibratile transducers in another of the four quadrants and are arranged symmetrically about the second axis with respect to yet another at least two vibratile transducers in yet another of the four quadrants.

18. The system of claim 15, wherein the at least two vibratile transducers secured to each of the four walls and are arranged symmetrically about one of the first axis and the second axis with respect to each other and are arranged symmetrically about the other of the first axis and the second axis with respect to another at least two vibratile transducers secured another of the four walls.

19. The system of claim 1, wherein causing the spatial centers of the aural and tactile stimuli to move in coordination with each other comprises causing the spatial centers of the aural and tactile stimuli to reside at a common location and to move in concert with one another along a shared path.

20. The system of claim 1, wherein causing the spatial centers of the aural and tactile stimuli to move in coordination with each other comprises causing the spatial centers of the aural and tactile stimuli to reside at different locations and to move in concert with one another along different paths.

* * * * *